(12) United States Patent
Cannon et al.

(10) Patent No.: US 7,485,133 B2
(45) Date of Patent: Feb. 3, 2009

(54) FORCE DIFFUSION SPINAL HOOK

(75) Inventors: Bradley J. Cannon, Memphis, TN (US); Hai H. Trieu, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 638 days.

(21) Appl. No.: 10/890,940

(22) Filed: Jul. 14, 2004

(65) Prior Publication Data
US 2006/0015099 A1 Jan. 19, 2006

(51) Int. Cl.
*A61B 17/70* (2006.01)

(52) U.S. Cl. .................. 606/276; 606/246; 606/279; 606/330; 606/76

(58) Field of Classification Search .............. 606/61, 606/86, 72, 246, 250, 276, 279, 302, 330, 606/76; 24/471, 598.4, 601.6
See application file for complete search history.

(56) References Cited

U.S. PATENT DOCUMENTS

| | | | |
|---|---|---|---|
| 3,741,205 A | 6/1973 | Markolf et al. | |
| 4,085,744 A * | 4/1978 | Lewis et al. | 623/17.11 |
| 4,274,401 A | 6/1981 | Miskew | |
| 4,338,926 A | 7/1982 | Kummer et al. | |
| 4,369,769 A | 1/1983 | Edwards | |
| 4,375,810 A | 3/1983 | Belykh et al. | |
| 4,403,606 A | 9/1983 | Woo et al. | |
| 4,409,968 A * | 10/1983 | Drummond | 606/61 |
| 4,655,222 A | 4/1987 | Florez et al. | |
| 4,943,292 A | 7/1990 | Foux | |
| 5,057,111 A | 10/1991 | Park | |
| 5,330,472 A | 7/1994 | Metz-Stavenhagen | |
| 5,476,464 A | 12/1995 | Metz-Stavenhagen et al. | |
| 5,496,321 A | 3/1996 | Puno et al. | |
| 5,540,689 A | 7/1996 | Sanders et al. | |
| 5,586,983 A | 12/1996 | Sanders et al. | |
| 5,591,234 A | 1/1997 | Kirsch | |
| 5,601,555 A | 2/1997 | Moskovich | |
| 5,609,593 A | 3/1997 | Errico et al. | |
| 5,779,707 A | 7/1998 | Bertholet et al. | |
| 5,824,088 A | 10/1998 | Kirsch | |
| 5,938,662 A | 8/1999 | Rinner | |
| 6,280,444 B1 | 8/2001 | Zucherman et al. | |
| 6,336,930 B1 | 1/2002 | Stalcup et al. | |
| 6,514,255 B1 * | 2/2003 | Ferree | 606/61 |
| 6,656,180 B2 | 12/2003 | Stahurski | |
| 2002/0133155 A1 | 9/2002 | Ferree | |
| 2005/0240194 A1 * | 10/2005 | Chappuis | 606/86 |

FOREIGN PATENT DOCUMENTS

EP 0 564 046 A1 10/1993

* cited by examiner

*Primary Examiner*—Eduardo C Robert
*Assistant Examiner*—Andrew Yang
(74) *Attorney, Agent, or Firm*—Krieg Devault

(57) ABSTRACT

A force diffusion hook includes a hook element and a connecting member receiving portion for receiving a connecting member to stabilize a spinal column segment. The hook element defines a receptacle for receiving a bony portion. A force diffusion member extends along the receptacle between the hook element and the bony portion. The force diffusion member is deformable to distribute load between the bony portion and the hook element.

50 Claims, 3 Drawing Sheets

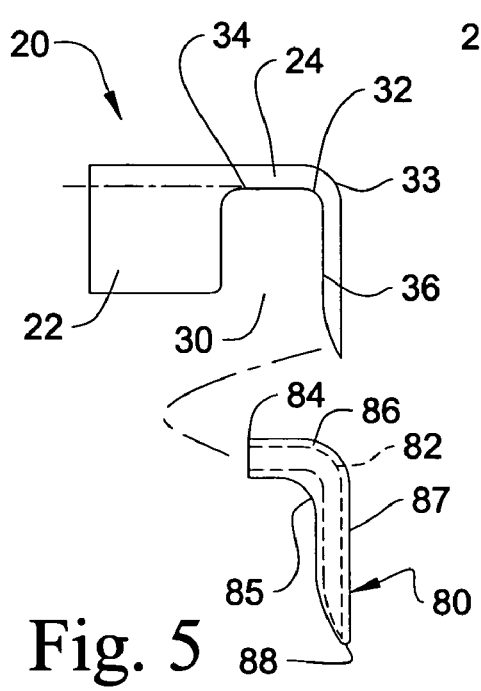
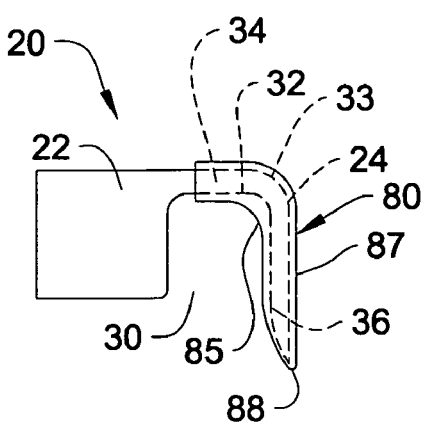
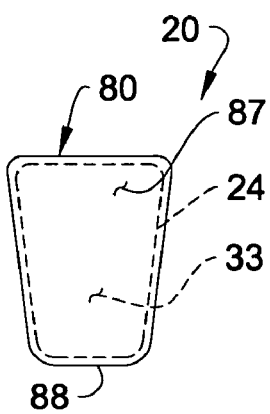
Fig. 5    Fig. 6    Fig. 7
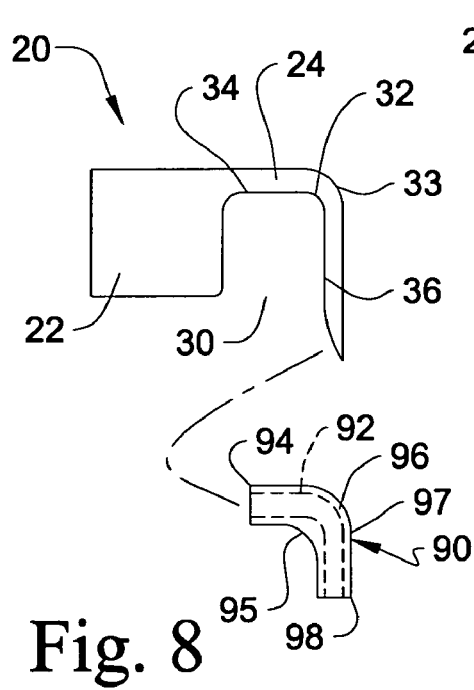
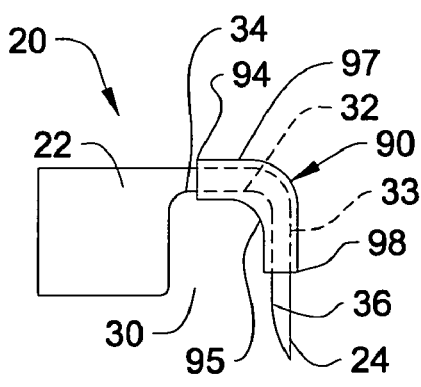
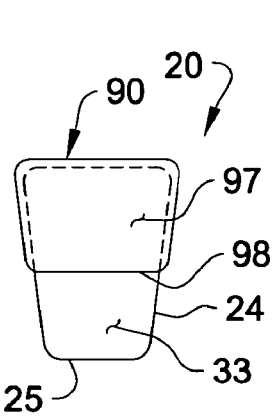
Fig. 8    Fig. 9    Fig. 10
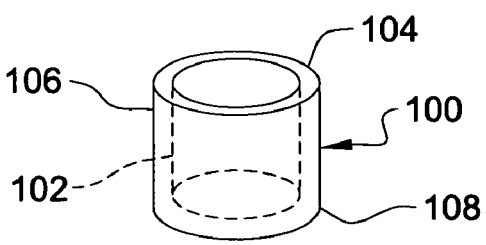
Fig. 11

US 7,485,133 B2

FORCE DIFFUSION SPINAL HOOK

BACKGROUND

The spine is subject to various pathologies that compromise its load bearing and support capabilities. Such pathologies of the spine include, for example, degenerative diseases, the effects of tumors and, of course, fractures and dislocations attributable to physical trauma. External stabilization systems have been secured to the spine for the treatment of such pathologies. Hooks and other fasteners may be employed to engage external stabilization devices to the bony portions of the spinal column. The complex and non-uniform anatomy of the spinal column can hinder the achievement of optimal contact and force distribution between fasteners and the bony elements to which the fasteners may be engaged.

SUMMARY

According to one aspect, a force diffusion hook includes a hook body with an connecting member engaging portion and a hook element extending from the connecting member engaging portion. The hook element includes a bone retaining surface defining a receptacle for receiving a bony portion. A deformable force diffusion member extends along the bone retaining surface adjacent the receptacle. The force diffusion member deforms to distribute loading between the hook element and the bony portion.

According to another aspect, a force diffusion hook includes a hook body with an connecting member engaging portion and a hook element extending therefrom. The hook element includes a bone retaining surface defining a receptacle for receiving a bony portion. A deformable force diffusion member extends along the bone retaining surface adjacent the receptacle. The force diffusion member includes a sleeve having a passage for receiving the hook element therein.

According to a further aspect, a force diffusion hook includes a hook body with an connecting member engaging portion and a hook element extending therefrom. The hook element includes a bone retaining surface that defines a receptacle for receiving a bony portion. The hook further includes force diffusing means extending along the bone retaining surface adjacent the receptacle for distributing loading from the bony portion to the hook element.

These and other aspects will also be apparent from the following description.

BRIEF DESCRIPTION OF THE FIGURES

FIG. 5 is an exploded view of another embodiment force diffusion hook.

FIG. 6 is an elevation view of the hook of FIG. 5.

FIG. 7 is a right hand side view of the hook of FIG. 6.

FIG. 8 is an exploded view of another embodiment force diffusion hook.

FIG. 9 is an elevation view of the hook of FIG. 8.

FIG. 10 is a right hand side view of the hook of FIG. 9.

FIG. 11 is a perspective view of another embodiment force diffusion member.

DESCRIPTION OF THE ILLUSTRATED EMBODIMENTS

Figures 1, 3:
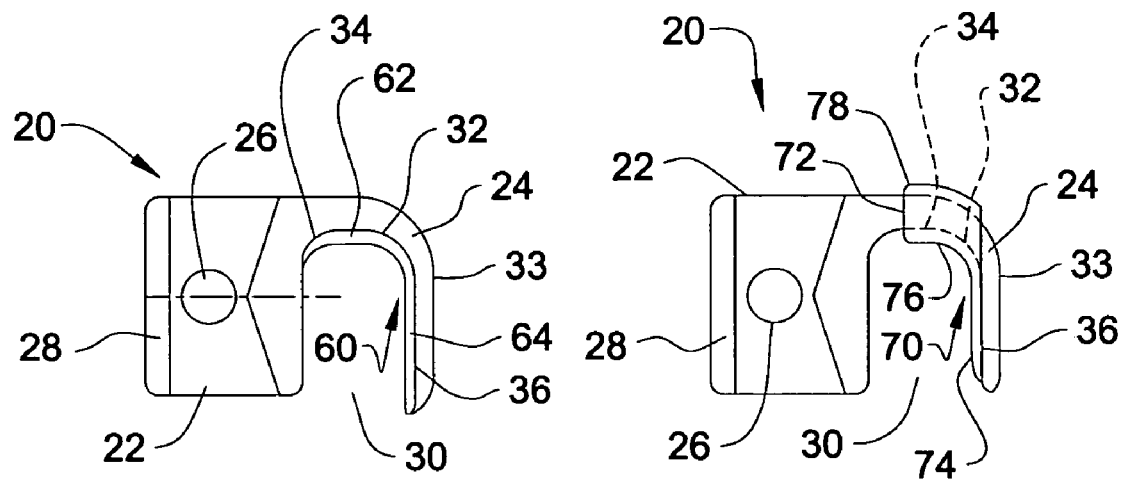
FIG. 1 is an elevation view of a force diffusion hook according to one embodiment.
FIG. 3 is an elevation view of another embodiment force diffusion hook.

For the purposes of promoting an understanding of the principles of the invention, reference will now be made to the embodiments illustrated in the drawings and specific language will be used to describe the same. It will nevertheless be understood that no limitation of the scope of the invention is hereby intended. Any such alterations and further modifications in the illustrated devices, and any such further applications of the principles of the invention as illustrated herein are contemplated as would normally occur to one skilled in the art to which the invention relates.

Spinal hooks include a hook element forming a receptacle to receive a bony portion of the spinal column. Spinal hooks also include a connecting member engaging portion for engagement with a connecting member that extends along one or more vertebrae of the spinal column. The bony portion engaged by the hook element can be the lamina, pedicle, spinous or transverse processes, or any other bony structure of a vertebra. The hook element couples the connecting member to the spinal column so that corrective forces to the vertebra can be applied or maintained through the connecting member and its engagement to one or more other vertebrae.

The hook element includes a rigid structure to facilitate the transfer of the loading between the connecting member and the bony portion. The spinal hook includes a force diffusion member along the receptacle and between the hook element and the bony portion. The force diffusion member is deformable to distribute the loading between the spinal hook and the bony portion.

The bony portion engaged by the hook element may include any one of a number of irregular shapes in view of the location of the bony portion along the spinal column, the portion of the vertebrae involved, the anatomy of the patient, and other factors. The rigid structure of the hook element may not allow optimal direct placement and contact between the bony portion and the hook element. For example, if a rigid hook element were placed in direct contact with the bony portion, the hook element may only contact isolated locations of the bony portion along the hook element due to irregular surface characteristics of the bony portion along the hook element. The force diffusion member between the hook element and the bony portion can conform to irregular surface profiles of the bony portion while maintaining intimate contact between the spinal hook and the bony portion. This distributes or diffuses the loading over an area of the bony portion in contact with the force diffusion member, reducing potential for cutting, crushing, cracking or otherwise deforming the bony portion.

Figures 2, 4:
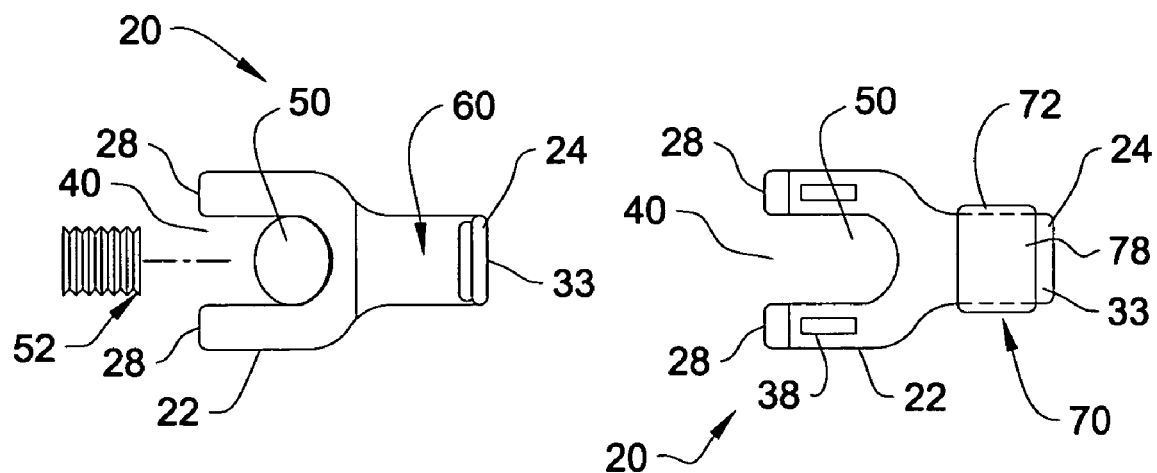
FIG. 2 is an end view of the hook of FIG. 1.
FIG. 4 is an end view of the hook of FIG. 3.

FIGS. 1 and 2 depict a spinal hook 20 including a connecting member engaging portion 22 and a hook element 24 extending from connecting member engaging portion 22. A force diffusion member 60 extends along at least one surface of hook element 24 that is adjacent a receptacle 30. Receptacle 30 is defined by hook element 24 and/or force diffusion member 60, and receives a bony portion of the spinal column therein. Force diffusion member 60 is deformable relative to hook element 24 and the bony portion received in receptacle 30 to adapt hook element 24 to the bony portion. Hook element 24 transmits loading between the connecting member engaged to connecting member engaging portion 22 and the bony portion.

A connecting member 50 is shown in section in FIG. 2. Connecting member 50 is positionable in a channel 40 formed along connecting member engaging portion 22. In the illustrated embodiment, channel 40 is U-shaped and formed by a pair of arms 28. Arms 28 include internal threads for engagement with a plug 52 illustrated in the form of an externally threaded set screw that is threadingly engageable to arms 28 to capture connecting member 50 in channel 40. Other embodiments contemplate other forms for connecting member engaging portion 22. For example, the channel can be enclosed, circular, open to one or both sides rather than top loading as shown, or offset laterally from hook element 24. Connecting member 50 can be rigid, elastic, bendable, or formable, and can be in the form of rod, tether, cable, plate, staple or other device positionable in, on or about connecting member engaging portion 22 and along one or more vertebrae of the spinal column. Plug 52 can be a set screw, cap, nut, wedge, or other device to engage connecting member 50 to connecting member engaging portion 22.

Connecting member engaging portion 22 may include oppositely opening recesses 26 formed in the outer surfaces of arms 28. Recesses 26 are circular in shape, and facilitate engagement of an instrument or other device to spinal hook 20. Such instruments may be employed for placement and manipulation of spinal hook 20 relative to a bony portion of the spinal column. As shown in FIG. 4, the ends of arms 28 may include rectangular recesses 38 to receive or facilitate engagement to other implants, instruments or devices. For example, compression, distraction and/or other alignment instruments can be engaged between multiple hooks along the spinal column to deliver compression or distraction forces between vertebrae through the spinal hooks. The connecting member 50 can then be engaged between hooks engaged to the vertebrae to maintain the compression, distraction or other alignment force that has been applied. Recesses 26, 38 may include any shape, and it is further contemplated that connecting member engaging portion 22 is provided without one or both of the recesses 26, 38.

Referring back to FIGS. 1 and 2, hook element 24 includes a bone retaining surface 32 oriented toward receptacle 30. Bone retaining surface 32 includes a first portion 34 extending from connecting member engaging portion 22 and a second portion 36 extending from first portion 34. First portion 34 extends transversely to connecting member 50 in channel 40, and can include a surface profile along receptacle 30 that is curved or otherwise shaped to extend along the bony portion received in receptacle 30. Other surface profile shapes for first portion 34 include one or more linear surfaces, angled surfaces, curved surfaces and combinations of linear, angled, and/or curved surfaces. Second portion 36 extends from first portion 34 along receptacle 30, and is spaced from connecting member engaging portion 22. Second portion 36 is shown with a linear surface profile, but may also include angled, curved surfaces and linear surface profiles alone or in combination with one another.

Force diffusion member 60 forms a layer of deformable material that extends along bone retaining surface 32, and includes a first portion 62 extending along first portion 34 of bone retaining surface 32 and a second portion 64 extending along second portion 36 of bone retaining surface 32. In the illustrated embodiment, first portion 62 is curved and second portion 64 is linear to mimic the shape of surface profile of bone retaining surface 32 along receptacle 30. Other forms for first and second portions 62, 64 are also contemplated, including those shapes that differ from the shape of the surface profile of bone retaining surface 32. Force diffusion member 60 can form a layer that entirely covers bone retaining surface 32, or that leaves one or more portions of bone retaining surface 32 exposed.

Other embodiments for the force diffusion member are also contemplated. For example, in FIGS. 3 and 4, there is shown force diffusion member 70 that includes a sleeve 72 and an extension portion 74 extending from sleeve 72. Sleeve 72 defines an inner passage for receiving hook element 24 therethrough so that a first side 76 of sleeve 72 is oriented toward receptacle 30 and extends along first portion 34 of bone retaining surface 32. Sleeve 72 further includes a second side 78 along outer surface 33 of hook element 24 opposite first portion 34. Second side 78 is oriented toward the soft tissue and away from the bony portion received in receptacle 30. When sleeve 72 is positioned about first portion 34 of bone retaining surface 32, extension portion 74 extends along second portion 36 of bone retaining surface 32. Extension portion 74 does not extend about outer surface 33 of hook element 24, but rather extends only along bone retaining surface 32 adjacent receptacle 30. The intrusion of hook element 24 and force diffusion member 70 into tissue along second portion 36 of bone retaining surface 32 is thus minimized.

Another embodiment force diffusion member 80 is shown in FIGS. 5-7. Force diffusion member 80 includes a sleeve 86 extending between a first end 84 and a second end 88. Sleeve 86 includes a passage 82 for receiving hook element 24 therein. Passage 82 is open at first end 84 and closed at second end 88 so that hook element 24 is substantially enclosed or encapsulated within sleeve 86. Sleeve 86 and passage 82 each include a shape that mimics the shape of hook element 24, which in the illustrated embodiment is an L shape with rounded transitions between the first and second portions 34, 36 of bone retaining surface 32. In the illustrated embodiment, sleeve 86 includes a first side 85 extending along bone retaining surface 32 adjacent receptacle 30, and an opposite second side 87 extending along outer surface 33 of hook element 24.

Another embodiment force diffusion member 90 is shown in FIGS. 8-10. Force diffusion member 90 includes a sleeve 96 extending between a first end 94 and a second end 98. Sleeve 96 includes a passage 92 for receiving hook element 24 therein. Passage 92 is open at first end 84 and also open at second end 98 so that hook element 24 is substantially enclosed or encapsulated within sleeve 96, but the terminal end 25 of hook element 24 protrudes from second end 98. Sleeve 96 and passage 92 each include a shape that mimics the shape of hook element 24, which in the illustrated embodiment is an L shape with rounded transitions between the first and second portions 34, 36 of bone retaining surface 32. In the illustrated embodiment, sleeve 96 includes a first side 95 extending along bone retaining surface 32 adjacent receptacle 30, and an opposite second side 97 extending along outer surface 33 of hook element 24.

Referring to FIG. 11, there is shown another embodiment force diffusion member 100. Force diffusion member 100 includes a sleeve 106 extending between a first end 104 and a second end 108. A passage 102 extends between and opens at first and second ends 104, 108. Sleeve 106 forms a cylindrical shape along its length, and can include a circular, oval, square, rectangular, non-circular, or any other cross-sectional shape. Hook element 24 is positionable in the opening of passage 102 adjacent first end 104, and sleeve 106 is movable along the hook element to position sleeve 100 along bone retaining surface 32 and outer surface 33. The deformability of sleeve 106 allows passage 102 to stretch and collapse as may be needed to conform to the shape of hook element 24 along bone retaining surface 32 and outer surface 33.

In the embodiments discussed above, the force diffusion member can be provided with characteristics that differ along bone retaining surface 32 and outer surface 33. For example, the portion of the force diffusion member along outer surface 33 can be more deformable or less abrasive than the portion of the force diffusion member along bone retaining surface 32. This provides additional protection to the soft tissue and other anatomical structures that may lie adjacent outer surface 33 from the wear that may be created by direct contact with hook element 24 or contact with the portion of the force diffusion member along bone retaining surface 32.

In another embodiment, the force diffusion member is comprised of at least two bands of material positioned about hook element 24. A first inner band is positioned adjacent bone retaining surface 32 and outer surface 33 and deforms to distribute or diffuse force to hook element 24. A second outer band extends about the first band and is conformable thereto. The second band includes properties that resists wearing of the force diffusion member against the bony portion received in receptacle 30.

Figure 12:
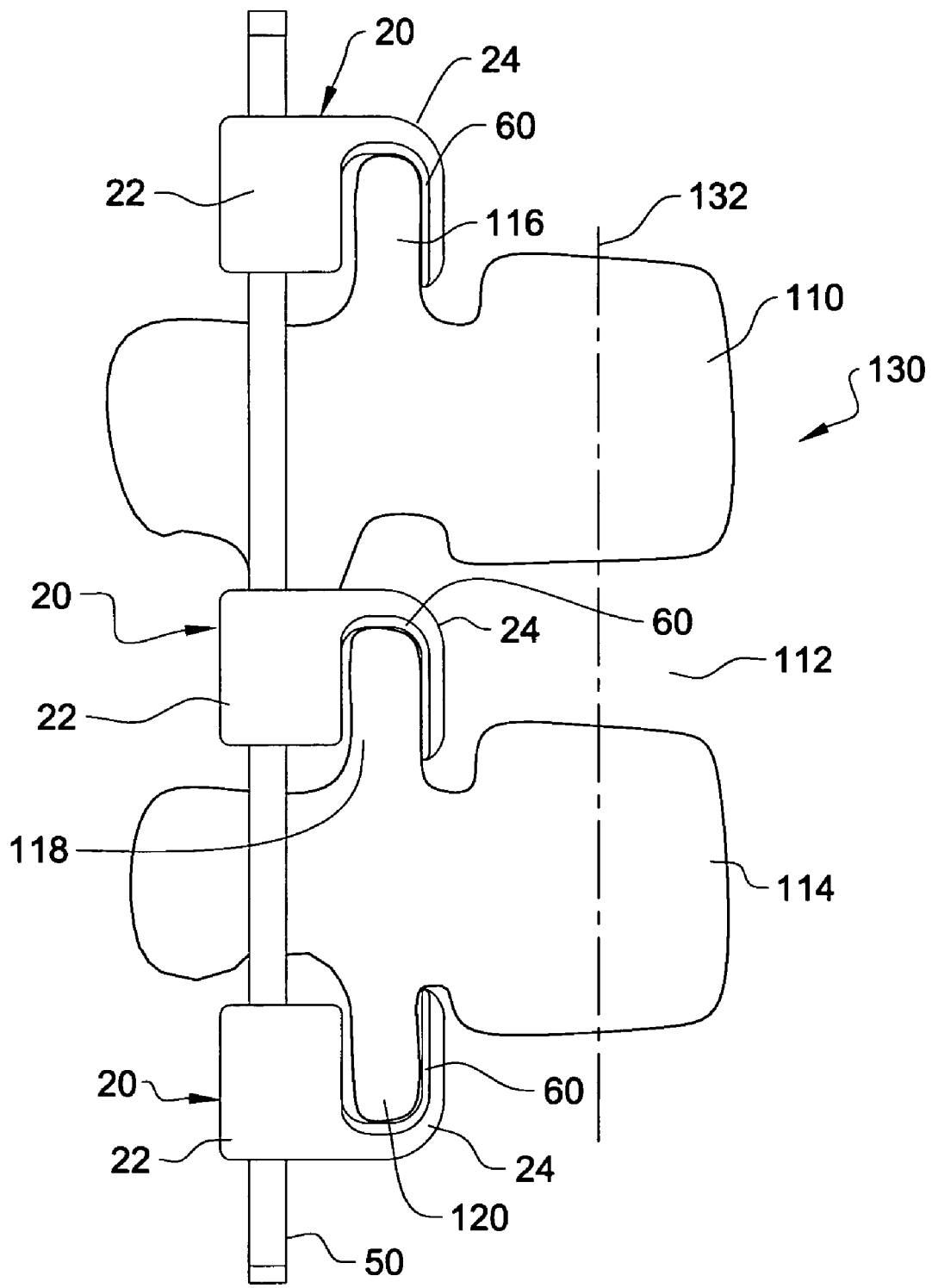
FIG. 12 is an elevation view of a portion of the spinal column with the force diffusion hooks of FIG. 1 engaged to the lamina to retain a connecting member in position relative to vertebrae of the spinal column.

FIG. 12 shows one application of force diffusion spinal hook 20 along the spinal column, such as along spinal column segment 130. In FIG. 12, spinal hooks 20 with force diffusion member 60 are shown, it being understood that any of the force diffusion members discussed herein could be employed with any one or combination of spinal hooks 20. Spinal column segment 130 includes a first vertebra 110, a second vertebra 114, and a disc space 112 therebetween. First vertebra 110 includes an upper lamina 116, and second vertebra 114 includes an upper lamina 118 and a lower lamina 120. Spinal hooks 20 are provided and positioned with hook elements 24 engaged to respective ones of the laminae 116, 118, 120. Connecting member 50 extends between and is engaged to connecting member engaging portions 22 of spinal hooks 20.

The spinal hooks 20 engaged to laminae 116, 120 can be secured to apply a clamping force between vertebra 110, 114. The spinal hook 20 engaged to lamina 118 can be provided to stabilize a position of vertebra 114 relative to vertebrae 110 to, for example, correct a misalignment of vertebra 114 relative to vertebra 110 along the spinal column axis 132. Force diffusion members 60 deform to distribute the clamping and alignment forces applied to the bony portions of the lamina, providing a greater surface area of contact between hook element 24 and the engaged lamina. The rigid portion of hook element 24 along which force diffusion member 60 extends transmits the applied forced to connecting member 50, which maintains the corrected or desired positioning between vertebrae 110, 114. It is also contemplated that connecting member 50 can be engaged along the spinal column with any suitable connectors in addition to at least one spinal hook 20, including, for example, screws, wires, staples, cables, plates, or other devices.

Hook element 24 can be made from any suitable material, including rigid materials such as stainless steel, titanium, and allows thereof. The force diffusion members can be made from any material that is deformable to better conform to the bony portion and distribute loading to hook element 24. The force diffusion members can be made from any suitable biocompatible material, including polymers, silicone, polyurethane, copolymers of silicone and polyurethane, polyetheretherketone, ultra high molecular weight polyethylene (UHMWPE), rubber, elastomers, hard and soft plastics, and composites thereof, for example.

The force diffusion members can be woven or braided with strands of deformable material alone or in combination with any other suitable material. The force diffusion members can also be provided in various forms, including a coating, solid members or sheets; braided members, sheets or sleeves; woven members, sheets or sleeves; composite members, sheets or sleeves; and one or more material layers, for example. The force diffusion members can be applied to hook element 24 via any one or combination of a powder coating, dip coating, spray coating, over-molding or bonding, slip fitting, friction fitting, gluing, fusing, welding, or mechanical fastening.

In one embodiment, hook element 24 is rigid in that its deformation under typical loading conditions associated with its engagement with the spinal column is minimal or non-existent. The force diffusion members, at least along bone retaining surface 32, are more deformable than hook element 24. The force diffusion members change in form in response to loading conditions of the spinal column to dampen the loading between the bony portion and hook element 24 and distribute or diffuse the loading to hook element 24. The deformation of the force diffusion member can also conform the force diffusion member to the bony portion, reducing stress risers that may be created in the bony portion and providing greater surface area of contact between the bony portion and the spinal hook. The force diffusion members can be elastic and return toward their unloaded form when loading is removed therefrom, or can be inelastic and retain their deformed shape after loading. In one embodiment, the force diffusion members include a thickness along bone retaining surface 32 that is at least 50 microns. Other thicknesses for the force diffusion members along bone retaining surface 32 are also contemplated.

While the invention has been illustrated and described in detail in the drawings and foregoing description, the same is to be considered as illustrative and not restrictive in character, it being understood that all changes and modifications that come within the spirit of the invention are desired to be protected.

What is claimed is:

1. A force diffusion hook, comprising:
a connecting member engaging portion and a hook element extending from said connecting member engaging portion, said hook element including a bone retaining surface defining a receptacle for receiving a bony portion, at least a portion of said bone retaining surface being spaced from said connecting member engaging portion with said receptacle therebetween, and further comprising a deformable force diffusion member extending along said bone retaining surface adjacent said receptacle, wherein said force diffusion member deforms to distribute loading between the bony portion and said hook element, and wherein said force diffusion member further extends along an outer surface of said hook element opposite said receptacle, a portion of said force diffusion member along said outer surface being more deformable in response to a loading than a portion of said first diffusion member along said receptacle.

2. The hook of claim 1, wherein said bone retaining surface includes a curved portion adjacent said connecting member engaging portion.

3. The hook of claim 1, wherein said force diffusion member comprises a sleeve including a passage for receiving said hook element.

4. The hook of claim 3, wherein said sleeve includes a first end and an opposite second end, and said passage extends between said first and second ends.

5. The hook of claim 4, wherein said passage opens at each of said first and second ends.

6. The hook of claim 4, wherein said passage is closed at said second end, said first end of said sleeve being positionable about said hook element with said closed end positioned adjacent a terminal end of said hook element.

7. The hook of claim 4, wherein said force diffusion member includes an extension portion extending from said second end of said sleeve and along a portion of said bone retaining member that is spaced from said connecting member engaging portion and extends along said receptacle.

8. The hook of claim 7, wherein said bone retaining surface includes a curved portion extending from said connecting member engaging portion, said sleeve being positioned about said curved portion.

9. The hook of claim 1, wherein said force diffusion member includes a thickness along said bone retaining surface of at least 50 microns.

10. The hook of claim 1, wherein said force diffusion member is comprised of a material selected from the group consisting of: silicone, polyurethane, copolymers of silicone and polyurethane, polyetheretherketone, polyester, and UHMWPE.

11. The hook of claim 1, wherein said force diffusion member includes a form selected from the group consisting of: a solid member, a braided member, a woven member, and a coating.

12. The hook of claim 1, further comprising means for securing said force diffusion member to said hook element.

13. The hook of claim 12, wherein said means for securing said force diffusion member to said hook element is selected from a group consisting of: gluing, fusing, friction fitting, powder coating, dip coating, spray coating, over molding, and fastening.

14. The hook of claim 1, wherein said force diffusion member is elastic.

15. The hook of claim 1, wherein said hook element is substantially non-deformable in response to said loading of said bony portion.

16. The hook of claim 1, wherein said bone retaining surface includes a curved portion adjacent said connecting member engaging portion and a linear portion extending from said curved portion along said receptacle.

17. A force diffusion hook, comprising:
a connecting member engaging portion and a hook element extending from said connecting member engaging portion, said hook element including a bone retaining surface defining a receptacle for receiving a bony portion, at least a portion of said bone retaining surface being spaced from said connecting member engaging portion with said receptacle therebetween, and further comprising a deformable force diffusion member extending along said bone retaining surface adjacent said receptacle, wherein said force diffusion member deforms to distribute loading between the bony portion and said hook element, wherein said force diffusion member comprises a sleeve including a first end, an opposite second end, and a passage extending between said first and second ends for receiving said hook element, and wherein said force diffusion member includes an extension portion extending from said second end of said sleeve and along a portion of said hook that is spaced from said connecting member engaging portion and extends along said receptacle.

18. The hook of claim 17, wherein said bone retaining surface includes a curved portion adjacent said connecting member engaging portion.

19. The hook of claim 17, wherein said passage opens at each of said first and second ends.

20. The hook of claim 17, wherein said bone retaining surface includes a curved portion extending from said connecting member engaging portion, said sleeve being positioned about said curved portion.

21. The hook of claim 17, wherein said force diffusion member includes a thickness along said bone retaining surface of at least 50microns.

22. The hook of claim 17, wherein said force diffusion member is comprised of a material selected from the group consisting of: silicone, polyurethane, copolymers of silicone and polyurethane, polyetheretherketone, polyester, and UHMWPE.

23. The hook of claim 17, wherein said force diffusion member includes a form selected from the group consisting of: a solid member, a braided member, a woven member, and a coating.

24. The hook of claim 17, further comprising means for securing said force diffusion member to said hook element.

25. The hook of claim 24, wherein said means for securing said force diffusion member to said hook element is selected from a group consisting of: gluing, fusing, friction fitting, powder coating, dip coating, spray coating, over molding, and fastening.

26. The hook of claim 17, wherein said force diffusion member is elastic.

27. The hook of claim 17, wherein said hook element is substantially non-deformable in response to said loading of said bony portion.

28. The hook of claim 17, wherein said bone retaining surface includes a curved portion adjacent said connecting member engaging portion and a linear portion extending from said curved portion along said receptacle.

29. The apparatus of claim 17, wherein said hook element includes a first portion extending transversely to said connecting member engaging portion and a second portion spaced from said connecting member engaging portion and extending transversely to said first portion, said bone retaining surface extending along both said first portion and said second portion, said second portion including first and second side surfaces bounding said bone retaining surface;
and wherein said force diffusion member contacts said first portion and said second portion, said force diffusion member contacting said second portion at said bone retaining surface between but not contacting said side surfaces.

30. A force diffusion hook, comprising:
a connecting member engaging portion and a hook element extending from said connecting member engaging portion, said hook element including a bone retaining surface defining a receptacle for receiving a bony portion, at least a portion of said bone retaining surface being spaced from said connecting member engaging portion with said receptacle therebetween, and further comprising a deformable force diffusion member extending along said bone retaining surface adjacent said receptacle, wherein said force diffusion member comprises a sleeve including a first end, an opposite second end, and a passage extending between said first and second ends for receiving said hook element therein, and wherein said force diffusion member includes an extension portion extending from said second end of said sleeve and along a portion of said hook element that is spaced from said connecting member engaging portion and extends along said receptacle.

31. The hook of claim 30, wherein said bone retaining surface includes a curved portion adjacent said connecting member engaging portion.

32. The hook of claim 30, wherein said passage opens at each of said first and second ends.

33. The hook of claim 30, wherein said bone retaining surface includes a curved portion extending from said connecting member engaging portion, said sleeve being positioned about said curved portion.

34. The hook of claim 30, wherein said force diffusion member includes a thickness along said bone retaining surface of at least 50 microns.

35. The hook of claim 30, wherein said force diffusion member is comprised of a material selected from the group consisting of: silicone, polyurethane, copolymers of silicone and polyurethane, polyetheretherketone, polyester, and UHMWPE.

36. The hook of claim 30, wherein said force diffusion member includes a form selected from the group consisting of: a solid member, a braided member, a woven member, and a coating.

37. The hook of claim 30, further comprising means for securing said force diffusion member to said hook element.

38. The hook of claim 37, wherein said means for securing said force diffusion member to said hook element is selected from a group consisting of: gluing, fusing, friction fitting, powder coating, dip coating, spray coating, over molding, and fastening.

39. The hook of claim 30, wherein said force diffusion member is elastic.

40. The hook of claim 30, wherein said hook element is substantially non-deformable in response to said loading of said bony portion.

41. The hook of claim 30, wherein said bone retaining surface includes a curved portion adjacent said connecting member engaging portion and a linear portion extending from said curved portion along said receptacle.

42. A force diffusion hook, comprising:
a connecting member engaging portion and a hook element extending from said connecting member engaging portion, said hook element including a bone retaining surface defining a receptacle for receiving a bony portion, at least a portion of said bone retaining surface being spaced from said connecting member engaging portion with said receptacle therebetween, and further comprising force diffusing means extending along said bone retaining surface adjacent said receptacle for distributing loading between the bony portion and said hook element, wherein said force diffusing means comprises a sleeve including a first end, an opposite second end and a passage extending between said first and second ends for receiving said hook element therein, and wherein said force diffusing means includes an extension portion extending from said second end of said sleeve and along a portion of said hook element that is spaced from said connecting member engaging portion and extends along said receptacle.

43. The hook of claim 42, wherein said bone retaining surface includes a curved portion adjacent said connecting member engaging portion.

44. The hook of claim 42, wherein said force diffusing means comprises a sleeve having a passage for receiving said hook element therein.

45. The hook of claim 42, wherein said passage opens at each of said first and second ends.

46. The hook of claim 42, wherein said hook element includes a curved portion extending from said connecting member engaging portion, said sleeve extending about said curved portion.

47. The hook of claim 42, wherein said force diffusing means includes a thickness along said bone retaining surface of at least 50microns.

48. The hook of claim 42, wherein said force diffusing means is comprised of a material selected from the group consisting of: silicone, polyurethane, copolymers of silicone and polyurethane, polyetheretherketone, polyester, and UHMWPE.

49. The hook of claim 42, wherein said force diffusing means is elastic.

50. The hook of claim 42, wherein said hook element is substantially rigid in response to said loading.

* * * * *